United States Patent [19]

Schroder et al.

[11] Patent Number: 4,570,014

[45] Date of Patent: Feb. 11, 1986

[54] CYCLOALKANECARBOXYLIC ACID COMPOUNDS

[75] Inventors: Rolf Schroder, Wuppertal; Klaus Lürssen, Berg. Gladbach, both of Fed. Rep. of Germany

[73] Assignee: Bayer Aktiengesellschaft, Leverkusen, Fed. Rep. of Germany

[21] Appl. No.: 330,915

[22] Filed: Dec. 15, 1981

Related U.S. Application Data

[60] Continuation of Ser. No. 192,744, Oct. 1, 1980, abandoned, which is a division of Ser. No. 38,153, May 11, 1979.

[30] Foreign Application Priority Data

Jun. 3, 1978 [DE] Fed. Rep. of Germany ....... 2824517
Feb. 20, 1979 [DE] Fed. Rep. of Germany ....... 2906507

[51] Int. Cl.[4] ............................................. C07C 69/74
[52] U.S. Cl. ................... 560/124; 260/501.11; 560/48; 560/122; 560/123; 560/125; 562/457; 562/504; 562/505; 562/506; 562/507; 564/152; 564/155; 564/189; 564/190; 564/191
[58] Field of Search ............... 560/122, 124, 125, 123, 560/115, 48; 260/501.11, 501.13; 564/189, 190, 123, 155, 152, 191; 562/504, 506, 507, 505, 457

[56] References Cited

U.S. PATENT DOCUMENTS

| | | | |
|---|---|---|---|
| 3,853,952 | 12/1974 | Kishida et al. | 71/106 |
| 3,923,491 | 12/1975 | O'Brien et al. | 71/106 |
| 4,102,672 | 7/1978 | Kida et al. | 71/106 |

OTHER PUBLICATIONS

Connors et al., J. Chem. Soc., pp. 2119–2132 (1960).
Cremlyn, J. Chem. Soc., pp. 3977–3980 (1962).
Schollkopf, Chem. Ser., 108, pp. 1580–1592 (1975).
Bregovec et al., Chem. Abst. 77, 113845(n).
Tailleur et al., Can. J. Chem., 39, pp. 1309–1320 (1961).
Schoellkopf et al., Chem. Abst. 79, 65844(d) (1973).

*Primary Examiner*—Michael L. Shippen
*Attorney, Agent, or Firm*—Felfe & Lynch

[57] ABSTRACT

Novel plant growth regulant composition comprising as an active ingredient at least one cycloalkanecarboxylic acid compound of the formula $$\underset{\underset{O}{\parallel}}{\overset{(CH_2)_n}{\diagdown}} \overset{R^1}{\underset{C-R,}{\diagup}} \quad (1)$$

in which
R is hydroxyl, alkoxy, aralkoxy, amino, alkylamino, dialkylamino or the radical $$O^\ominus M^\oplus$$

wherein
$M^\oplus$ is one alkali metal ion equivalent or alkaline earth metal ion equivalent, or an ammonium, alkylammonium, dialkylammonium, trialkylammonium or tetraalkylammonium ion,
$R^1$ is amino or the radical $$-NH-\underset{\underset{O}{\parallel}}{C}-R^2$$

wherein
$R^2$ is hydrogen, alkyl or aryl, or
$R^1$ is the radical $-N^\oplus H_3 X^\ominus$,
wherein $X^\ominus$ is chloride, bromide or iodide, and n is 1, 2, 3, 4 or 5, in admixture with a solid or liquefied gaseous diluent or carrier or in admixture with a liquid diluent or carrier containing a surface-active agent.

23 Claims, No Drawings

CYCLOALKANECARBOXYLIC ACID COMPOUNDS

This is a continuation of Ser. No. 192,744 filed Oct. 1, 1980 (now abandoned) which is in turn a division of application Ser. No. 038,153 filed May 11, 1979.

The present invention relates to compositions and methods for regulating plant growth. More specifically, the invention relates to such methods and compositions utilizing certain cycloalkane-carboxylic acid compounds.

It is already known that (2-chloroethyl)-trimethylammonium chloride has plant growth-regulating properties (see U.S. Pat. No. 3,156,554). However, the activity of this substance is not always completely satisfactory, especially when low amounts are used.

It is further known that a product, commercially available under the name "Off-Shoot-T", based on fatty alcohols with 6, 8, 10 and 12 carbon atoms can be employed for regulating plant growth, in particular for suppressing the growth of side shoots in tobacco (see Farm. Chem. Handbook 1975, Meister Publishing Co., Willoughby, Ohio, 1975 and Pesticide Dictionary D 147). Nevertheless, in some cases, especially when low amounts are used, the activity of this product also leaves something to be desired.

It is also already known that 2-chloroethylphosphonic acid can be used as a plant growth regulator (see German Offenlegungsschrift (German Published Specification) No. 2,050,245). However, its action is also not completely satisfactory when low amounts are used.

It has now been found that cycloalkane-carboxylic acid derivatives of the general formula

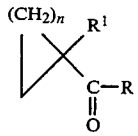

in which
R represents hydroxyl, alkoxy, aralkoxy, amino, alkylamino, dialkylamino or the radical $$O^{\ominus} M^{\oplus}$$

wherein
$M^{\oplus}$ represents one alkali metal ion equivalent or alkaline earth metal ion equivalent, or an ammonium, alkylammonium, dialkylammonium, trialkylammonium or tetraalkylammonium ion,
$R^1$ represents amino or the radical

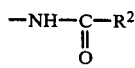

wherein
$R^2$ represents hydrogen, alkyl or aryl, or
$R^1$ represents the radical $-NH_3X^{\ominus}$,
wherein
$X^{\ominus}$ represents chloride, bromide or iodide, and
n represents 1, 2, 3, 4 or 5, are very suitable for regulating plant growth.

Accordingly, the present invention provides a plant growth-regulating composition containing as active ingredient a compound of the formula (I) in admixture with a solid or liquefied gaseous diluent or carrier or in admixture with a liquid diluent or carrier containing a surface-active agent.

The invention also provides a method of regulating the growth of plants which comprises applying to the plants, or to a habitat thereof, a compound of the formula (I) alone or in the form of a composition containing as active ingredient a compound of the present invention in admixture with a diluent or carrier.

Preferably, in the formula (I), R represents hydroxyl, alkoxy with 1 to 20 carbon atoms, benzyloxy, amino, alkylamino with 1 to 4 carbon atoms, dialkylamino with 1 to 4 carbon atoms per alkyl radical or the radical $$O^{\ominus} M^{\oplus}$$

wherein
$M^{\oplus}$ represents a sodium or potassium ion, one magnesium ion equivalent or calcium ion equivalent, ammonium, alkylammonium with 1 to 4 carbon atoms or dialkylammonium, trialkylammonium or tetraalkylammonium with in each case 1 to 4 carbon atoms per alkyl radical,
$R^1$ represents amino or the radical $-NH-CO-R^2$,
wherein
$R^2$ represents hydrogen, alkyl with 1 to 4 carbon atoms or phenyl, or
$R^1$ represents the radical $-N^{\oplus}H_3Cl^{\ominus}$, and
n represents 1 or 2.

Surprisingly, the cycloalkanecarboxylic acid derivatives of the formula (I), used according to the invention, exhibit a considerably higher plant growth-regulating action than the substances (2-chloroethyl)-trimethylammonium chloride, Off-Shoot-T and 2-chloroethylphosphonic acid, which are known from the state of the art and are active compounds of high activity which have the same type of action. The substances which can be used according to the invention thus represent a valuable enrichment of the art.

Very particularly preferred compounds of the formula (I) are those in which
R represents hydroxyl, alkoxy with 1 to 10 carbon atoms, benzyloxy, amino, alkylamino with 1 or 2 carbon atoms, dialkylamino with 1 or 2 carbon atoms per alkyl radical or the radical $$O^{\ominus} M^{\oplus}$$

wherein
$M^{\oplus}$ represents a sodium or potassium ion, one magnesium ion equivalent or calcium ion equivalent, ammonium, alkylammonium with 1 or 2 carbon atoms or dialkylammonium, trialkylammonium or tetraalkylammonium with in each case 1 or 2 carbon atoms per alkyl radical,
$R^1$ represents amino, formylamino, acetylamino, propionylamino, benzoylamino or $-NH_3^{\oplus}Cl^{\ominus}$, and
n represents 1 or 2.

Examples which may be mentioned of compounds of the formula (I) are: α-amino, α-formylamino-, α-acetylamino- and α-benzoylamino-cyclopropanecarboxylic acid and -cyclobutanecarboxylic acid, the sodium, potassium, magnesium, calcium, ammonium, methylammonium, ethylammonium, dimethylammonium, diethylammonium, trimethylammonium, triethylammonium, tetramethylammonium and tetraethylammonium salts thereof, furthermore the methyl, ethyl and benzyl esters thereof and the amides, methylamides, ethylamides, dimethylamides and diethylamides thereof; and also α-amino-cyclopropane- and α-amino-cyclobutane-carboxylic acid methyl ester hydrochloride, ethyl ester hydrochloride, propyl ester hydrochloride, butyl ester hydrochloride, pentyl ester hydrochloride, hexyl ester hydrochloride, octyl ester hydrochloride and benzyl ester hydrochloride, and α-amino-cyclopropane- and α-amino-cyclobutane-carboxylic acid hydrochloride.

Some of the compounds of the formula (I) are known (see Liebigs Ann. Chem. 1973, 611–618; Chem. Ber. 108 (1975), 1580–1592 and J. Chem. Soc. 1960, 2119–2132 and 1962, 3977–3980).

Some of the compounds which can be used according to the invention have not been described in the literature. These new compounds are characterised by the general formula

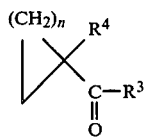 (Ia)

in which

R³ represents alkoxy, aralkoxy, amino, alkylamino, dialkylamino or the radical

wherein

M⊕ represents one alkali metal ion equivalent or alkaline earth metal ion equivalent, or an ammonium, alkylammonium, dialkylammonium, trialkylammonium or tetraalkylammonium ion, R⁴ represents amino or the radical

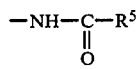

wherein

R⁵ represents hydrogen (provided R³ does not represent ethoxy), alkyl (provided R³ does not represent methoxy) or aryl, or R⁴ represents the radical —N⊕H₃X⊖ wherein

X⊖ represents iodide, bromide or (provided R³ does not represent ethoxy) chloride, and n represents 1, 2, 3, 4 or 5.

The new compounds (Ia) can be prepared by several processes. Thus, (a) those cycloalkanecarboxylic acid derivatives of the formula (Ia) in which R⁴ represents formylamino are obtained when α-isocyano-cycloalkanecarboxylic acid derivatives of the general formula

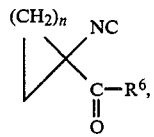 (II)

in which

R⁶ represents alkoxy, except for ethoxy, aralkoxy, amino, alkylamino, dialkylamino or the radical

O⊕M⊖, wherein

M⊕ represents one alkali metal ion equivalent or alkaline earth metal ion equivalent, or an ammonium, alkylammonium, dialkylammonium, trialkylammonium or tetraalkylammonium ion, and n has the meaning stated above, are hydrolysed with water, if appropriate in the presence of a catalyst and if appropriate in the presence of an additional diluent, (b) those cycloalkanecarboxylic acid derivatives of the formula (Ia) in which R⁴ represents formylamino and R³ represents OM, wherein M represents an alkali metal ion, are obtained when α-isocyano-cycloalkanecarboxylic acid derivatives of the general formula

in which

R⁷ represents alkyl and n has the meaning stated above, are reacted with alkali metal hydroxides under mild conditions, if appropriate in the presence of an additional diluent, and the α-isocyano-carboxylic acid salts thereby formed, of the general formula

in which

M' represents an alkali metal ion and n has the meaning stated above, are hydrolysed by boiling with aqueous alcohol, (c) those cycloalkanecarboxylic acid derivatives of the formula (Ia) in which R⁴ represents formylamino and R³ represents OM, wherein M has the meanings stated above excluding an alkali metal ion, are obtained when α-formylamino-cycloalkanecarboxylic acid salts which can be prepared according to process (b), of the general formula

in which

M' and n have the meanings stated above, are treated with an equivalent amount of a strong acid, if appropriate in the presence of a diluent, and the α-formylamino-cycloalkanecarboxylic acids thereby formed, of the general formula $$\underset{\substack{|\\ \text{C—OH,}\\ \|\\ \text{O}}}{\overset{(CH_2)_n}{\diagdown}}\!\!\!\!\!\!\diagup^{\text{NH—CHO}} \qquad (Ic)$$

in which n has the meaning stated above, are reacted with compounds of the general formula $$M''OR^8 \qquad (V),$$

in which

M'' represents an alkaline earth metal ion, an ammonium or mono-, di-, tri- or tetra-alkyl-ammonium ion and $R^8$ represents hydrogen, methyl or ethyl, if appropriate in the presence of a diluent, (d) those cycloalkanecarboxylic acid derivatives of the formula (Ia) in which $R^4$ represents formylamino and $R^3$ represents amino, alkylamino or dialkylamino are obtained when α-isocyano-carboxylic acid salts, which can be prepared according to process (b), of the formula $$\underset{\substack{|\\ \text{C—OM',}\\ \|\\ \text{O}}}{\overset{(CH_2)_n}{\diagdown}}\!\!\!\!\!\!\diagup^{\text{NC}} \qquad (IV)$$

in which

M' and n have the meanings stated above, are reacted with compounds of the general formula $$\text{H—N}\!\!\diagup_{R^{10}}^{R^9} \qquad (VI)$$

in which $R^9$ and $R^{10}$ are identical or different and represent hydrogen or alkyl, in the presence of hydrochloric acid and if appropriate in the presence of a diluent, (e) those compounds of the formula (Ia) in which $R^3$ represents alkoxy or aralkoxy and $R^4$ represents the radical —N⊕H$_3$X⊖, where X⊖ represents iodide, bromide or, if $R^3$ does not represent ethoxy, chloride, are obtained when α-formylaminocycloalkanecarboxylic acid derivatives, which can be prepared according to process (a), of the general formula $$\underset{\substack{|\\ \text{C—OR}^{11},\\ \|\\ \text{O}}}{\overset{(CH_2)_n}{\diagdown}}\!\!\!\!\!\!\diagup^{\text{NH—CHO}} \qquad (Id)$$

in which $R^{11}$ represents alkyl or aralkyl and n has the meaning stated above, are reacted with compounds of the general formula $$H^{\oplus}X^{\ominus} \qquad (VII),$$

in which

X⊖ has the meaning stated above, if appropriate in the presence of a diluent, (f) those cycloalkanecarboxylic acid derivatives of the formula (Ia) in which $R^4$ represents the radical —NH—CO—$R^5$ are obtained when α-aminocycloalkanecarboxylic acid derivatives of the general formula $$\underset{\substack{|\\ \text{C—R}^3,\\ \|\\ \text{O}}}{\overset{(CH_2)_n}{\diagdown}}\!\!\!\!\!\!\diagup^{\text{NH}} \qquad (Ie)$$

in which $R^3$ and n have the meanings stated above, are reacted with acylating agents of the general formula $$R^{12}\!\!-\!\!\underset{\|}{\overset{O}{C}}\!\!-\!\!Y, \qquad (VIII)$$

in which $R^{12}$ represents hydrogen, alkyl or aryl and

Y represents chlorine or the radical —O—CO—$R^{12}$, in which $R^{12}$ has the above-mentioned meaning, in the presence of an acid acceptor and if appropriate in the presence of a diluent, and (g) those cycloalkanecarboxylic acid derivatives of the formula (Ia) in which $R^4$ represents amino are obtained when α-aminocycloalkanecarboxylic acid chlorides of the general formula $$\underset{\substack{|\\ \text{C—Cl,}\\ \|\\ \text{O}}}{\overset{(CH_2)_n}{\diagdown}}\!\!\!\!\!\!\diagup^{\text{NH}_2} \qquad (IX)$$

in which n has the meaning stated above, are reacted with compounds of the general formula $$R^3H \qquad (X),$$

in which $R^3$ has the meaning indicated above, if appropriate in the presence of an acid-binding agent and if appropriate in the presence of a diluent.

Preferred new cycloalkanecarboxylic acid derivatives are those compounds of the formula (Ia) in which $R^3$ represents alkoxy with 1 to 20 (especially 1 to 10) carbon atoms, benzyloxy, amino, alkylamino with 1 to 4 (especially 1 or 2) carbon atoms, dialkylamino with 1 to 4 (especially 1 or 2) carbon atoms per alkyl radical or the radical $$O^{\ominus}M^{\oplus}$$

wherein

M⊕ represents a sodium or potassium ion, one magnesium ion equivalent or calcium ion equivalent, ammonium, alkylammonium with 1 to 4 (especially 1 or 2) carbon atoms or dialkylammonium, trialkylammonium or tetraalkylammonium, in each case with 1 to 4 (especially 1 or 2) carbon atoms per alkyl radical, and R⁴ represents amino or the radical —NH—CO—R⁵ wherein R⁵ represents hydrogen (provided R³ does not represent ethoxy), alkyl with 1 to 4 carbon atoms (but not methyl if R³ represents methoxy) or phenyl, or R⁴ represents —N⊕H₃Cl⊖ (provided R³ does not represent ethoxy).

If, for example, α-isocyano-cyclopropanecarboxylic acid methyl ester and aqueous alcoholic hydrochloric acid are used as the reactants in process (a), α-isocyano-cyclopropanecarboxylic acid methyl ester and sodium hydroxide in ethanol are used as the reactants in process (b), sodium α-formylamino-cyclopropanecarboxylate and concentrated hydrochloric acid are used as the reactants in the first stage of process (c) and an aqueous alcoholic calcium hydroxide solution is used as the reactant in the second stage, sodium α-isocyano-cyclopropanecarboxylate and concentrated ammonia in combination with concentrated hydrochloric acid are used as the reactants in process (d), α-formylamino-cyclopropanecarboxylic acid methyl ester and dilute hydrochloric acid are used as the reactants in process (e), α-amino-cyclopropanecarboxylic acid and benzoyl chloride are used as the reactants in process (f) and α-aminocyclopropanecarboxylic acid chloride and diethylamine are used as the reactants in process (g), the reactions can be represented by the equations which follow:

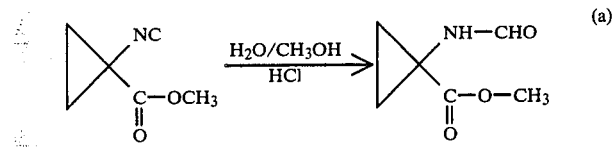
(a)

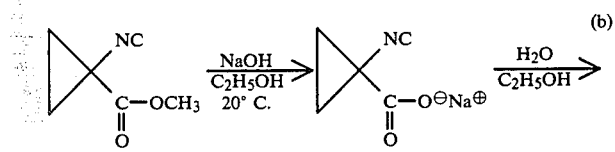
(b)

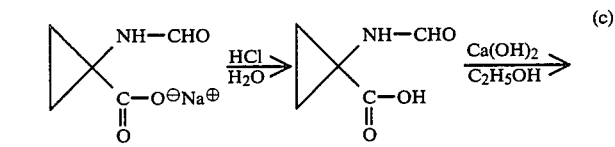
(c)

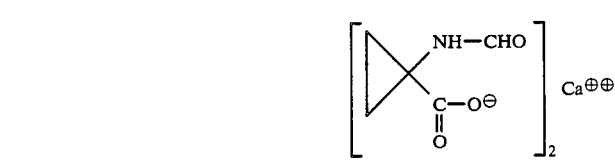

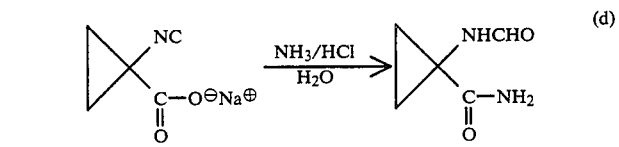
(d)

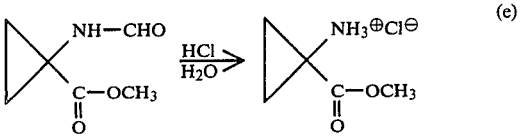
(e)

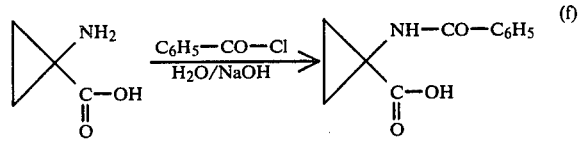
(f)

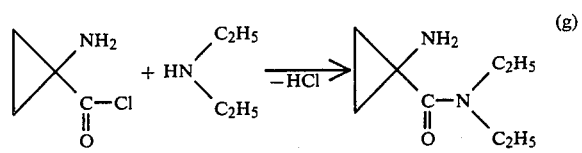
(g)

The formulae (II) and (III) provide general definitions of the α-isocyano-cycloalkanecarboxylic acid derivatives to be used as starting substances in processes (a) and (b) according to the invention. In the formula (II), R⁶ preferably represents alkoxy with 1 or with 3 to 20 (especially 3 to 10) carbon atoms, benzyloxy, amino, alkylamino with 1 to 4 (especially 1 or 2) carbon atoms, dialkylamino with 1 to 4 (especially 1 or 2) carbon atoms per alkyl radical or the radical O⊖M⊕, wherein M⊕ represents a sodium or potassium ion, one magnesium ion equivalent or calcium ion equivalent, ammonium, alkylammonium with 1 to 4 (especially 1 or 2) carbon atoms or dialkylammonium, trialkylammonium or tetraalkylammonium with in each case 1 to 4 (especially 1 or 2) carbon atoms per alkyl radical. R⁷ in the formula (III) preferably represents alkyl with 1 to 3 carbon atoms, in particular methyl or ethyl. In the formulae (II) and (III), n in each case preferably represents 1 or 2.

The α-isocyano-cycloalkanecarboxylic acid derivatives of the formulae (II) and (III) are already known, or they can be prepared by processes which are known in principle (see DT-OS (German Published Specification) No. 2,063,502; Angew. Chem. 83, (1971), 357–358; Chem. Ber. 108 (1975), 1580–1592 and Liebigs Ann. Chem. 1973, 611–618).

The formulae (V), (VI), (VII), (VIII) and (X) provide general definitions of the compounds to be used as reactants in processes (c) to (g) according to the invention. In the formula (V), M" preferably represents those radicals which have already been mentioned as preferred for M in connection with the description of the α-isocyano-cycloalkanecarboxylic acid derivatives of the formula (II), however M" does not represent an alkali metal ion. In the formula (VI), R⁹ and R¹⁰ independently of one another preferably represent hydrogen or alkyl with 1 to 4 (especially 1 or 2) carbon atoms. In the formula (VII), X preferably represents chlorine. In the formula (VIII), R¹² preferably represents hydrogen, alkyl with 1 to 4 carbon atoms or phenyl. In the formula (X), R³ preferably represents those radicals which have already been mentioned as preferred for R³ in connection with the description of the compounds of the formula (Ia) according to the invention. The compounds of the formulae (V), (VI), (VII), (VIII) and (X) are already known.

The formula (Ie) provides a general definition of the α-amino-cycloalkanecarboxylic acid derivatives to be used as starting substances in process (f) according to the invention. In this formula, $R^3$ preferably represents those radicals which have already been mentioned as preferred for $R^3$ in connection with the description of the compounds of the formula (Ia) according to the invention. The compounds of the formula (Ie) can be prepared by process (g) according to the invention.

The formula (IX) provides a definition of the α-amino-cycloalkanecarboxylic acid chlorides to be used as starting substances in process (g) according to the invention. The compounds of the formula (IX) have not yet been described in the literature, but they can be prepared by converting the corresponding acids into the acid chlorides by customary methods, for example with thionyl chloride. The necessary α-amino-cycloalkanecarboxylic acids on which the compounds of the formula (IX) are based are known, or they can be prepared by known methods (see J. Org. Chem. 29 (1964), 2764–2766; Synthesis 1978, 46 and J. Chem. Soc. 1960, 2119–2132 and 1962, 3977–3980).

In general, preparative process (a) is carried out in an aqueous solution or in a diluent which contains water and an organic solvent, such as, for example, alcohol, dioxan or tetrahydrofuran. The reaction can be carried out under acid catalysis, for example with hydrochloric acid as the catalyst. The reaction temperature can be varied within a substantial range. In general, the reaction is carried out at temperatures between 0° and 100° C., preferably at 10° to 40° C. if a catalyst is used and otherwise preferably at 60° to 90° C.

Isolation of the products in process (a) is effected by customary methods; the reaction mixture is extracted with a water-immiscible solvent, for example with methylene chloride, the organic phase is dried and filtered and the solvent is distilled off from the filitrate in vacuo. The crude products which remain can be purified by distillation or if appropriate by recrystallisation.

In general, process (b) is carried out using one or more organic solvents. Possible organic solvents are, in particular: ethers, such as diethyl ether, dibutyl ether, tetrahydrofuran and dioxan, ketones, such as acetone, methyl ethyl ketone, methyl isopropyl ketone and methyl isobutyl ketone, nitriles, such as acetonitrile and propionitrile, and alcohols, such as methanol, ethanol and propanol. In general, the reaction is carried out at temperatures between 0° and 100° C., preferably at 5° to 25° C. in the first reaction step and preferably at 25° to 90° C. in the second stage.

The process can be carried out in two isolated reaction steps or as a "one-pot process". In general, the α-isocyano-cycloalkanecarboxylic acid derivative to be employed as a starting substance is dispersed in one of the solvents indicated, and an alcoholic alkali metal hydroxide solution which contains 1 to 1.2 moles of hydroxide per mole of carboxylic acid derivatives is added. The α-isocyano-cycloalkanecarboxylic acid salts initially formed in general crystallise out on prolonged stirring of the mixture and can be isolated by filtration. In general, these intermediates are further converted by boiling with aqueous alcohol which contains 1 to 1.2 moles of water per mole of α-isocyano-cycloalkanecarboxylic acid salt. Working up is effected, for example, by adding ether to the cooled reaction mixture and filtering off the α-formylamino-cycloalkanecarboxylic acid salt which has thereby crystallised out.

For carrying out process (c), in general the α-formylamino-cycloalkanecarboxylic acid salts to be employed are dissolved in water, and the equimolar amount of concentrated hydrochloric acid is added. The reaction is carried out at temperatures between 0° and 30° C. The products, which crystallise out after the reaction mixtures have stood for a relatively long period, can be isolated by filtration. In general, alcohols, in particular methanol and ethanol, are used as solvents in carrying out the second stage of process (c). 1 mole of the base of the formula (V) is employed per mole of α-formylamino-cycloalkanecarboxylic acid. The reaction is carried out at temperatures between 10° and 40° C. After stirring the reaction mixture for a short time, the solvent is distilled off in vacuo, the residue is triturated with ether and the product is filtered off and dried.

In general, up to 3 moles of ammonia or amine of the formula (VI) and 1 mole of hydrochloric acid are employed per mole of α-isocyano-cycloalkanecarboxylic acid derivative for carrying out process (d). The reaction is in general carried out using water as the solvent and at temperatures between 0° and 40° C. After stirring the reaction mixture for several hours, volatile components and the solvent are distilled off in vacuo. The crude product which remains is worked up by customary methods, for example by extraction with methylene chloride, drying and filtration of the methylene chloride phase and concentration of the filtrate.

Process (e) is usually carried out using aqueous hydrochloric acid as the reaction medium. In general, the α-formylamino-cycloalkanecarboxylic acid derivatives to be employed as starting substances are stirred therein at room temperature for several days or are refluxed therein for several hours. The mixture is then evaporated to dryness in vacuo and the crystalline products which remain are dried over phosphorus pentoxide in a dessicator.

Water is generally used as the solvent in process (f). 1 to 1.2 moles of acylating agent and 2 to 2.5 moles of acid acceptor are employed per mole of α-amino-cycloalkanecarboxylic acid derivative. Acylating agents which are preferably used are: acetic anhydride, acetyl chloride, propionic anhydride, propionyl chloride and benzoyl chloride. Acid acceptors which are preferably used are alkali metal hydroxides, such as sodium hydroxide and potassium hydroxide, or alkali metal carbonates and bicarbonates, such as sodium carbonate and sodium bicarbonate.

The reaction according to process (f) is carried out at temperatures between 10° and 40° C. After stirring the reaction mixture for a short time, the pH is adjusted to 1 with a strong acid, such as, for example, hydrochloric acid. The products thereby obtained in the crystalline form can be isolated by filtration and purified by recrystallisation.

Possible diluents in process (g) according to the invention are water and inert organic solvents. However, in many cases, component (X) employed in excess can also function as the diluent.

Any of the customary acid acceptors can be used as the acid-binding agent in process (g) according to the invention. However, the reactant of the formula (X) employed in excess appropriately functions as the acid-binding agent.

The reaction temperatures can be varied within a substantial range in process (g) according to the invention. In general, the reaction is carried out at temperatures between 0° C. and 40° C., preferably between 10° C. and 25° C.

In carrying out process (g) according to the invention, about 1 to 2 moles of a compound of the formula (X) and if appropriate 1 mole of acid-binding agent are employed per mole of α-amino-cycloalkanecarboxylic acid chloride of the formula (IX). Working up is effected by customary methods.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth permits denser planting of the crop, so that a greater yield per area of ground can be achieved.

A further mechanism for increasing the yield by means of growth inhibitors is based on the fact that the nutrients benefit blossoming and fruit formation to a greater extent, whilst vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favourably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the sheeding of fruit—for example in the case of table fruit—in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound and very fine capsules in polymeric substances, coating compositions for use on seed, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other known active compounds, such as fungicides, insecticides; acaricides and herbicides, and also as mixtures with fertilisers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomising, scattering, dusting, foaming and gassing. Furthermore it is possible to apply the active compounds in accordance with the ultra-low-volume method, to spread the active compound preparation or the active compound itself on plants or parts of plants or to inject the active compound preparation or the active compound itself into the soil. It is also possible to treat the seeds of plants.

The active compound concentrations can be varied within a substantial range. In general, 0.01 to 50 kg, preferably 0.05 to 10 kg, of the active compound are employed per hectare of soil surface.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The plant-growth-regulating activity of the compounds of this invention is illustrated by the following biotest Examples.

In these Examples, the compounds according to the present invention are each identified by the number (given in brackets) of the corresponding preparative Example, which will be found later in this specification.

The known comparison compounds are identified as follows:

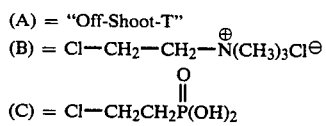

EXAMPLE A

Inhibition of growth of side shoots of tobacco

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Tobacco plants were grown in a greenhouse until the 7th foliage leaf had unfolded. In this stage, the apical vegetative tips of the plants were removed and the plants were sprayed with the preparations of active compound until dripping wet. After 3 weeks, the side shoots of the plants were broken off and weighed. The weight of the side shoots of the treated plants was compared with that of the untreated control plants. 100% inhibition denoted the absence of side shoots and 0% denoted a growth of side shoots which corresponded to that of the control plants.

The active compounds, active compound concentrations and results can be seen from the table which follows.

TABLE A

Inhibition of growth of side shoots of tobacco

| Active compound | Active compound concentration in % | Inhibition of growth in % |
|---|---|---|
| — (control) | — | 0 |
| (A) | 0.2 | 20 |
| (2) | 0.2 | 64 |

EXAMPLE B

Inhibition of growth of barley

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Barley plants were grown to the 2-leaf stage in a greenhouse. In this stage, the plants were sprayed with the preparations of active compound until dripping wet. After 3 weeks, the additional growth was measured on all plants and the inhibition of growth in % of the additional growth of the control plants was calculated. 100% meant that growth had stopped and 0% denoted a growth corresponding to that of the control plants.

The active compounds, active compound concentrations and results can be seen from the table which follows.

TABLE B

Inhibition of growth of barley

| Active compound | Active compound concentration in % | Inhibition of growth in % |
|---|---|---|
| — (control) | — | 0 |
| (2) | 0.05 | 25 |
| (3) | 0.05 | 30 |

EXAMPLE C

Inhibition of growth of wheat

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentrations with water.

Wheat plants were grown to the 2-leaf stage in a greenhouse. In this stage, the plants were sprayed with the preparations of active compound until dripping wet. After 3 weeks, the additional growth was measured on all plants and the inhibition of growth in % of the additional growth of the control plants was calculated. 100% meant that growth had stopped and 0% denoted a growth corresponding to that of the control plants.

The active compounds, active compound concentrations and results can be seen from the table which follows.

TABLE C

Inhibition of growth of wheat

| Active compound | Active compound concentration in % | Inhibition of growth in % |
|---|---|---|
| — (control) | — | 0 |
| (3) | 0.05 | 45 |
| (11) | 0.05 | 30 |

EXAMPLE D

Inhibition of growth of soya beans

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth was measured on all the plants and the inhibition of growth in % of the additional growth of the control plants was calculated. 100% meant that growth had stopped and 0% denoted a growth corresponding to that of the control plants.

The active compounds, active compound concentrations and results can be seen from the table which follows.

TABLE D

Inhibition of growth of soya beans

| Active compound | Active compound concentration in % | Inhibition of growth in % |
|---|---|---|
| — (control) | — | 0 |
| (B) | 0.05 | 0 |
| (2) | 0.05 | 85 |
| (3) | 0.05 | 75* |
| (4) | 0.05 | 25 |

*Plants exhibited a dark green coloration

EXAMPLE E

Acceleration of ripening of tomatoes

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Tomatoes were grown in a greenhouse in the usual manner, until about 30% of the fruits were ripe. In this stage, the plants were sprayed with the preparations of active compound until dripping wet. After various intervals of time, the number of ripe fruits on the individual test plants was determined and calculated in percent of the total number of fruits on the test plants concerned. Thus, 100% meant that all the fruits were ripe.

The results of this test can be seen from the table which follows.

TABLE E

| | Acceleration of ripening of tomatoes | | | |
|---|---|---|---|---|
| Active compound | Active compound concentration in % | Ripe fruits in % after | | |
| | | 2 days | 4 days | 7 days |
| — (control) | — | 37 | 40 | 44 |
| (C) | 0.1 | 46 | 57 | 79 |
| (2) | 0.1 | 53 | 65 | 86 |

EXAMPLE F

Stimulation of ethylene biosynthesis

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Pieces of leaf of identical size were punched from soya bean leaves. A constant number of pieces of leaf was incubated for 1 hour in Petri dishes which were filled with 10 ml of the active compound preparations or with corresponding control solutions without active compounds. Thereafter, the pieces of leaf were introduced into vessels which were closed air-tight, together with 1 ml of the particular preparation of active compound or control solution. After 24 hours the ethylene which had collected in the vessels was determined by customary methods of detection. The evolution of ethylene from the pieces of leaf treated with the preparations of active compound was compared with the evolution of ethylene of the controls.

In the table which follows:
0 denotes no action
+ denotes slight stimulation of ethylene biosynthesis
++ denotes moderate stimulation of ethylene biosynthesis
+++ denotes high stimulation of ethylene biosynthesis This test was particularly suitable for illustrating the growth-regulating properties of the compounds according to the invention.

The plant hormone ethylene affects numerous processes during the development of the plants. An increase in ethylene biosynthesis, such as can be achieved with the substances according to the invention, makes it possible to control these processes. The following may be mentioned here as examples in which there is, in particular, commercial interest: detachment of fruit, acceleration of ripening of fruit and leaves, induction of flowering, germination of seeds, thinning-out of fruit, stimulation of latex flux, for example in Hevea, influencing of gender and inhibition of growth, for example also to prevent the lodging of cereals.

The active compounds and the results can be seen from the table which follows.

TABLE F

| | Stimulation of ethylene biosynthesis | |
|---|---|---|
| Active compound | Active compound concentration in % | Action |
| — (control) | — | 0 |
| (B) | 0.001 | 0 |
| (2) | 0.001 | ++ |

TABLE F-continued

| | Stimulation of ethylene biosynthesis | |
|---|---|---|
| Active compound | Active compound concentration in % | Action |
| (3) | 0.001 | +++ |
| (5) | 0.001 | + |
| (8) | 0.001 | + |
| (10) | 0.001 | ++ |
| (11) | 0.001 | + |
| (14) | 0.001 | +++ |
| (15) | 0.001 | +++ |
| (16) | 0.001 | +++ |
| (17) | 0.001 | +++ |
| (21) | 0.001 | +++ |
| (26) | 0.001 | ++ |
| (20) | 0.001 | +++ |
| (24) | 0.001 | +++ |
| (6) | 0.001 | +++ |
| (7) | 0.001 | ++ |
| (18) | 0.001 | +++ |
| (19) | 0.001 | +++ |
| (22) | 0.001 | +++ |
| (23) | 0.001 | +++ |

PREPARATIVE EXAMPLES

EXAMPLE 1

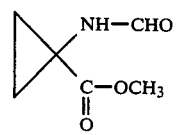
(1)

0.3 ml of concentrated hydrochloric acid and a solution of 5 g (0.04 mol) of α-isocyano-cyclopropanecarboxylic acid methyl ester in 10 ml of methanol were added successively to 40 ml of water at 20° C. The reaction mixture was stirred for 6 hours. It was then extracted twice with 50 ml of methylene chloride each time, the organic phase was dried over magnesium sulphate and filtered and the solvent was distilled off from the filtrate in vacuo. 4 g (70% of theory) of α-formylamino-cyclopropanecarboxylic acid methyl ester remained in the form of a colorless liquid.

Refractive index: $n_D^{20} = 1.4730$.

EXAMPLE 2

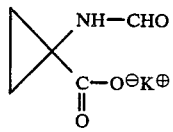
(2)

A solution of 3.1 g (0.55 mol) of potassium hydroxide in 50 ml of ethanol was added dropwise to a solution of 7 g (0.05 mol) of α-isocyano-cyclopropanecarboxylic acid ethyl ester in 100 ml of ether at 50° C. The mixture was stirred at 20° C. for 12 hours. After filtering off the precipitate and washing it with ether, 6.4 g (86% of theory) of potassium α-isocyano-cyclopropanecarboxylate were obtained as a white powder.

Melting point: 225° C.

1.18 g (0.66 mol) of water were added to a suspension of 9 g (0.06 mol) of potassium α-isocyano-cyclopropanecarboxylate in 50 ml of ethanol. The mixture was heated to the boil under reflux for 12 hours and, after cooling, 50 ml of ether were added at 20° C. After filtering of the precipitate, 7 g (70% of theory) of potassium α-formylaminocyclopropanecarboxylate were obtained in the form of white crystals.

Melting point: 186° C.

EXAMPLE 3

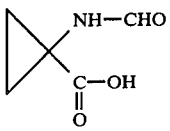 (3)

8.36 g (0.05 mol) of potassium α-formylamino-cyclopropanecarboxylate were dissolved in 20 ml of water, and 5 g (0.05 mol) of concentrated hydrochloric acid were added at 0° C. The mixture was left to stand at 5° C. overnight. After filtering off the precipitate and drying it, 5.2 g (80% of theory) of α-formylamino-cyclopropanecarboxylic acid were obtained in the form of colourless crystals.

Melting point: 189° C.

EXAMPLE 4

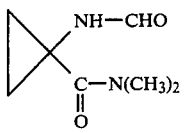 (4)

7.46 g (0.05 mol) of potassium α-isocyano-cyclopropanecarboxylate were added to a solution of 6.7 g (0.15 mol) of dimethylamine in 50 ml of water at 20° C., whilst stirring. After cooling the reaction mixture to 5° C., 5 g (0.05 mol) of concentrated hydrochloric acid were added and the mixture was left to stand at 20° C. in a closed reaction vessel for 12 hours. The volatile components were stripped off under a water pump vacuum at a bath temperature of 60° C. The product was extracted from the residue with methylene chloride; the solution was dried with magnesium sulphate and, after filtration, the solvent was distilled off from the filtrate in vacuo. 5.5 g (70% of theory) of α-formylamino-cyclopropanecarboxylic acid N,N-dimethylamide remained in the form of a light yellow liquid.

Refractive index: $n_D^{20} = 1.4350$.

EXAMPLE 5

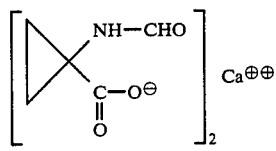 (5)

0.74 g (0.01 mol) of calcium hydroxide was added to a mixture of 2.5 g (0.02 mol) of α-formylamino-cyclopropanecarboxylic acid and 40 ml of ethanol at 25° C., whilst stirring, and the mixture was subsequently stirred at room temperature for a further 12 hours. The solution was then evaporated in vacuo and the residue was triturated with ether. After filtering off the solid and drying it, 2.6 g (97% of theory) of calcium α-formylamino-cyclopropanecarboxylate were obtained in the form of a white powder.

Melting point: 290° C.

EXAMPLE 6

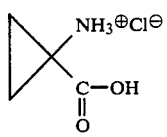 (6)

A mixture of 19.4 g (0.15 mol) of α-formylaminocyclopropane-carboxylic acid and 200 ml of 18% strength hydrochloric acid was heated to the boil under reflux for 3 hours. It was then evaporated to dryness in vacuo and the solid which remained was dried over phosphorus pentoxide in a vacuum desiccator.

Yield: 18 g (92% of theory) of α-amino-cyclopropanecarboxylic acid hydrochloride.

Melting point: 232° C.

EXAMPLE 7

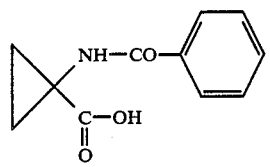 (7)

3.1 g (0.022 mol) of benzoyl chloride were added to a mixture of 2 g (0.02 mol) of α-amino-cyclopropanecarboxylic acid, 25 ml of water and 2.55 g (0.044 mol) of potassium hydroxide at 20° C., whilst stirring. After stirring the mixture for 30 minutes, it was acidified to pH 1 with concentrated hydrochloric acid and the precipitate was filtered off. For purification, the product was boiled up with 30 ml of water.

Yield: 2.1 g (51% of theory) of α-benzoylamino-cyclopropanecarboxylic acid.

Melting point: 209° C.

The compounds of the formula

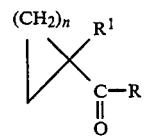 (I)

listed in the table below could be prepared analogously to one of Examples 1 to 7:

| Example No. | n | R | R¹ | Yield (% of theory) | Refractive index $n_D^{20}$ melting point (°C.); or boiling point (°C./mbars) |
|---|---|---|---|---|---|
| 8 | 1 | 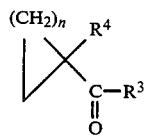 OCH₂—C₆H₅ | NHCHO | 74 | 1.5079 |
| 9 | 2 | O⁻K⁺ | NHCHO | 31 | 100 (decomposition) |
| 10 | 1 | O⁻HN(C₂H₅)₃⁺ | NHCHO | 85 | 1.4461 |
| 11 | 1 | OC₂H₅ | NHCHO | 71 | 110/0.1 |
| 12 | 1 | NH₂ | NHCHO | 70 | 145 |
| 13 | 2 | OC₂H₅ | NHCHO | 24 | 65/4 |
| 14 | 1 | OCH₃ | NH₃⁺Cl⁻ | 81 | 180 |
| 15 | 1 | OCH₃ | NH₂ | 77 | 1.4491 |
| 16 | 1 | OCH₂—C₆H₅ | NH₃⁺Cl⁻ | 51 | 92 |
| 17 | 1 | OCH₂—C₆H₅ | NH₂ | 86 | 1.4849 |
| 18 | 1 | O⁻Na⁺ | NH₂ | 97 | 216 |
| 19 | 1 | OH | NH₂ | 75 | 220 |
| 20 | 1 | OC₂H₅ | NH₃⁺Cl⁻ | 83 | 108 |
| 21 | 1 | OC₂H₅ | NH₂ | 75 | 1.4440 |
| 22 | 1 | O⁻K⁺ | NHCOCH₃ | 82 | 246 |
| 23 | 1 | OC₂H₅ | NHCOCH₃ | 90 | 76 |
| 24 | 1 | O(CH₂)₇CH₃ | NHCHO | 95 | 1.4321 |
| 25 | 1 | O(CH₂)₇CH₃ | NH₃⁺Cl⁻ | 91 | 1.4429 |
| 26 | 1 | O⁻Na⁺ | NHCHO | 90 | 221 |
| 27 | 1 | OC₄H₉—tert. | NH₃⁺Cl⁻ | 73 | 108 |

It will be understood that the specification and examples are illustrative but not limitative of the present invention and that other embodiments within the spirit and scope of the invention will suggest themselves to those skilled in the art.

What is claimed is:

1. Cycloalkanecarboxylic acid compound of the formula

(1a)

in which

R³ is alkoxy with 1 to 20 carbon atoms, amino, alkylamino with 1 to 4 carbon atoms dialkylamino with 1 to 4 carbon atoms in each alkyl radical or the radical

O⁻M⁺ wherein

M⊕ is sodium or potassium ion, one magnesium ion equivalent or one calcium ion equivalent; or an ammonium, alkylammonium with 1 to 4 carbon atoms; dialkylammonium, trialkylammonium or tetraalkylammonium ion in each case with 1 to 4 carbon atoms in each alkyl radical; and R⁴ is amino or the radical

—NH—C—R⁵
‖
O wherein

R⁵ is hydrogen with a proviso that R³ is other than ethoxy; or

R⁵ is alkyl with 1 to 4 carbon atoms with a proviso that R³ is other than methoxy or benzyloxy; or R⁴ is the radical N⊕H₃Cl⊖ with the proviso that R³ is other than ethoxy; and n is 1 or 2.

2. Cycloalkanecarboxylic acid compound as claimed in claim 1 wherein R³ is alkoxy with from 1 to 10 carbon atoms.

3. Cycloalkanecarboxylic acid compounds as claimed in claim 1 wherein R³ is benzyloxy.

4. Cycloalkanecarboxylic acid compounds as claimed in claim 1 wherein R³ is amino 5. Cycloalkanecarboxylic acid compounds as claimed in claim 1 wherein R³ is alkylamino with 1 to 4 carbon atoms.

6. Cycloalkanecarboxylic acid compounds as claimed in claim 1 wherein R³ is dialkylamino with 1 to 4 carbon atoms in each alkyl.

7. Cycloalkanecarboxylic acid compounds as claimed in claim 1 wherein R³ is the radical O⁻M⁺.

8. Cycloalkanecarboxylic acid compound as claimed in claim 7 wherein M⊕ is a sodium or potassium ion.

9. Cycloalkanecarboxylic acid compound as claimed in claim 7 wherein $M^\oplus$ is one magnesium ion equivalent or one calcium ion equivalent.

10. Cycloalkanecarboxylic acid compound as claimed in claim 7 wherein $M^+$ is an ammonium.

11. Cycloalkanecarboxylic acid compound as claimed in claim 7 wherein $M^\oplus$ is an alkylammonium with 1 to 4 carbon atoms.

12. Cycloalkanecarboxylic acid compound as claimed in claim 7 wherein $M^\oplus$ is a dialkylammonium with 1 to 4 carbon atoms in each alkyl radical.

13. Cycloalkanecarboxylic acid compound as claimed in claim 7 wherein $M^\oplus$ is a trialkylammonium with 1 to 4 carbon atoms in each alkyl radical.

14. Cycloalkanecarboxylic acid compound as claimed in claim 7 wherein $M^\oplus$ is a tetraalkyl ammonium ion with 1 to 4 carbon atoms in each alkyl radical.

15. Cycloalkanecarboxylic acid compound as claimed in claim 1 wherein $R^4$ is amino.

16. Cycloalkanecarboxylic acid compound as claimed in claim 1 wherein $R^4$ is the radical $-NH-C=O-R^5$.

17. Cycloalkanecarboxylic acid compound as claimed in claim 16 wherein $R^5$ is hydrogen, with a proviso that $R^3$ is other than ethoxy.

18. Cycloalkanecarboxylic acid compound as claimed in claim 16 wherein $R^5$ is alkyl, with a proviso that $R^3$ is other than methoxy or benzyloxy.

19. Cycloalkanecarboxylic acid compound as claimed in claim 1 wherein $R^4$ is the radical $-NH_3^\oplus Cl^\ominus$.

20. Cycloalkanecarboxylic acid compound as claimed in claim 1 wherein n is 1.

21. Cycloalkanecarboxylic acid compound as claimed in claim 1 wherein n is 2.

22. Cycloalkanecarboxylic acid compound as claimed in claim 1 designated potassium α-formylaminocyclopropanecarboxylate.

23. Cycloalkanecarboxylic acid compound as claimed in claim 1, designated alpha-formyl-amino-cyclopropane carboxylic acid n-octyl ester.

* * * * *